United States Patent [19]

Holzhauer et al.

[11] Patent Number: 4,786,752

[45] Date of Patent: Nov. 22, 1988

[54] CATALYST RECOVERY AND RECYCLE OF CATALYSTS IN PSEUDOCUMENT OXIDATION PROCESS

[75] Inventors: Juergen K. Holzhauer; Wayne P. Schammel, both of Naperville; Neal R. Nowicki, St. Charles, all of Ill.

[73] Assignee: Amoco Corporation, Chicago, Ill.

[21] Appl. No.: 92,479

[22] Filed: Sep. 3, 1987

Related U.S. Application Data

[63] Continuation-in-part of Ser. No. 781,935, Sep. 30, 1985, abandoned, which is a continuation-in-part of Ser. No. 565,915, Dec. 27, 1983, abandoned.

[51] Int. Cl.$^4$ .......................................... C07C 51/265
[52] U.S. Cl. .................................... 562/414; 502/24; 502/25; 502/28
[58] Field of Search .................. 562/414; 502/24, 25, 502/28

[56] References Cited

U.S. PATENT DOCUMENTS

| | | | |
|---|---|---|---|
| 4,488,999 | 12/1984 | Feld | 562/414 |
| 4,490,297 | 12/1984 | Feld | 562/414 |
| 4,490,298 | 12/1984 | Feld | 562/414 |
| 4,587,355 | 5/1986 | Brown | 562/414 |

*Primary Examiner*—Michael L. Shippen
*Attorney, Agent, or Firm*—Gunar J. Blumberg; William H. Magidson; Ralph C. Medhurst

[57] ABSTRACT

A method is disclosed for recovery and recycle of metal catalyst components of a catalyst from the liquid-phase oxidation of pseudocumene in the presence of an oxidation catalyst comprising cobalt, manganese, and bromine components or cobalt, manganese, zirconium and bromine components wherein said catalyst components are recovered by oxalate precipitation from aqueous residue.

6 Claims, No Drawings

CATALYST RECOVERY AND RECYCLE OF CATALYSTS IN PSEUDOCUMENT OXIDATION PROCESS

This application is a continuation-in-part application of Ser. No. 781,935, filed Sept. 30, 1985, now abandoned, which is a continuation-in-part application of Ser. No. 565,915 filed on Dec. 27, 1983, now abandoned.

BACKGROUND

The field of this invention relates to the recovery of the cobalt from the catalyst used in liquid-phase oxidation of pseudocumene to trimellitic acid.

SUMMARY OF THE INVENTION

Our novel process relates to the recovery of trimellitic acid (TMLA) catalyst components by oxalate precipitation as oxalate salts from aqueous residue obtained by dehydration of trimellitic acid to trimellitic anhydride, which is the product of the process. The recovered salts can be recycled to the oxidation reactor.

DETAILED DESCRIPTION OF THE INVENTION

Because of the high cobalt consumption of the TMLA reaction, a catalyst recovery is very advantageous. Aqueous extraction from residue does not work for TMLA because the TMLA residue is very soluble in water and because the metals are complexed with aromatic acids. Water is formed as a by-product in oxidation of pseudocumene to TMLA.

It has now been discovered that almost all of the cobalt is recovered from an aqueous solution of TMA dehydration residue by precipitation with oxalic acid. The TMA residue can be solvent stripper bottoms, product distillation bottoms, or a combination of the two, or total reactor effluent (TRE) distillation bottoms. At the normal boiling point, the TMA residue is soluble in as little as its own weight of water. Addition of oxalic acid gives a precipitate which is easily recovered by filtration or centrifugation. This precipitate can be used to replace part or all of the cobalt in the oxidation catalyst. Other catalyst components may have to be added to obtain the desired catalyst composition. An especially desirable feature of the novel process is the fact that manganese and zirconium recovery is not quantitative and bromine recovery is very low, allowing staged addition of these components to the oxidation.

Advantageously, the reclaimed catalyst is subjected to a heat treatment at 400°–550° F. in acetic acid prior to recycle to the oxidation to improve the activity and selectivity of the catalyst.

Suitable solvents for use in the process for the oxidation of pseudocumene to trimellitic acid include any $C_2$–$C_{16}$ fatty acids such as acetic acid, propionic acid, n-butyric acid, isobutyric acid, n-valeric acid, trimethylacetic acid and caproic acid and water and mixtures thereof. Preferably, the solvent is a mixture of acetic acid and water, which more preferably contains from 1 to 20 weight percent of water, as introduced into the oxidation reactor. The weight ratio of the solvent to pseudocumene introduced into the reactor in the liquid-phase oxidation of this invention is in the range of from about 0.5:1 to about 6:1, preferably from about 1:1 to about 4:1.

The source of molecular oxygen for the oxidation of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing less than about 8 volume percent oxygen (measured on a solvent-free basis).

The catalyst employed in the method of this invention comprises cobalt, manganese, and bromine components and optionally may include zirconium. The weight ratio of cobalt (calculated as elemental cobalt) in the cobalt component of the catalyst to the alkyl aromatic in the liquid-phase oxidation of the method of this invention is in the range of from about 0.5 to about 10 milligram atoms (mga) per gram mole of the alkyl aromatic. The weight ratio of manganese (calculated as elemental manganese) in the manganese component of the catalyst to cobalt (calculated as elemental cobalt) in the cobalt component of the catalyst in the liquid-phase oxidation of the method of this invention is in the range of from about 0.2 to about 10 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid-phase oxidation of the method of this invention is in the range of from about 0.2 to about 1.5 mga per mga of total cobalt and manganese.

At least a portion of the cobalt component introduced into the liquid-phase oxidation is reclaimed by oxalate precipitation as described hereafter.

The remainder, if any, of the total amount of cobalt component of the catalyst employed in the liquid-phase oxidation of this invention is introduced into the oxidation reactor as forms of cobalt that are soluble in the solvent.

In the event that soluble forms of the cobalt components are introduced into the liquid-phase oxidation of this invention, each of the cobalt components can be provided in any of its known ionic or combined forms that are soluble in the solvent. For example, when the solvent is an acetic acid medium, cobalt carbonate, acetate tetrahydrate, and/or bromide can be employed. The 0.2 to 1.5:1.0 elemental bromine-to-total cobalt and manganese milligram atom ratio is provided by a source of bromine. Such bromine sources include elemental bromine ($Br_2$), or ionic bromide (for example HBr, NaBr or KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-dibromide, etc.). The total bromine in molecular bromine and ionic bromine is used to determine satisfaction of the elemental bromine-to-total cobalt and manganese milligram atom ratio of 0.2–1.5:1.0. The bromide ion released from the organic bromides at the oxidation operating conditions can be readily determined by known analytical means. Tetrabromoethane, for example, at operating temperatures such as 170° to 225° C. has been found to yield about 3 effective gram atoms of bromine per gram mole.

In operation, the minimum pressure at which the reactor is maintained is that pressure which will maintain a substantial liquid phase of the pseudocumene and at least 70 percent of the solvent. The alkyl aromatics and solvent not in the liquid phase because of vaporization are removed from the reactor as a vapor-gas mixture, condensed and then returned to the reactor in the recycle solvent. When the solvent is an acetic acid-water mixture, suitable reaction gauge pressures are in the range of from about 0 kg/cm$^2$ to about 35 kg/cm$^2$, and typically are in the range of from about 10 kg/cm$^2$ to about 30 kg/cm$^2$.

The temperature range within the reactor is generally from about 120° C., preferably from about 150° C., to about 240° C., preferably to about 230° C.

In the preferred embodiment, generally, at least a major portion of the trimellitic acid and/or anhydride is separated from the product stream before the oxalic acid or oxalate salt is introduced into the product stream. In one version of the process, the total reactor effluent stream is subjected to a heat soak during which the acetic acid and water are distilled off and the bulk of the trimellitic acid is dehydrated to trimellitic anhydride. The crude product thus obtained is distilled with the trimellitic anhydride going overhead, leaving a molten bottoms stream containing some of the bromine and essentially all the catalyst metals. The catalyst metals are thereupon recovered from the bottoms stream.

In another version of the process, the oxidation reactor effluent is cooled to crystallize most of the trimellitic acid, which is separated by filtration. The filtrate is distilled to recover the acetic acid solvent, leaving a molten bottoms stream containing some of the catalyst metals and bromine. The wet trimellitic acid filter cake is thermally dehydrated to trimellitic anhydride. The crude product thus obtained is distilled with the trimellitic anhydride going overhead, leaving a molten bottoms stream containing the remaining catalyst metals and some bromine. The two residue streams containing the catalyst metals are usually combined, but they can be used separately for the process of our invention. The catalyst metals are thereupon recovered.

Molten bottoms residue streams obtained from either process are mixed with water in a ratio of about 0.1:1 to about 2:1, preferably about 0.3:1 to 1.5:1. Oxalic acid or a metal oxalate are added as solids or in an aqueous solution. Stoichiometrically, one mole of oxalic acid and/or of the oxalate ion can react with one gram atom of each of the cobalt or manganese ion to form the corresponding hydrated salt. However, since the extent of this reaction is influenced by the concentration of the reactants, the pH and temperature of the medium, the presence of oxygen and other factors, the number of moles of oxalic acid and other factors, the number of moles of oxalic acid and/or oxalate ion to be added per gram atom of total cobalt and manganese content of the stream needed to attain the desired recovery of cobalt and manganese which are a function of the overall composition, pH, and temperature of the stream and falls in the range of about 0.5:1 to about 3:1.

The oxalic acid or oxalate salt can be added to the bottoms residue streams before, during, or after the water addition. The process can be carried out in batch, semi-continuous, or continuous mode. Preferably, it is carried out at or near the atmospheric boiling point of the mixture, or about 220° F.

The precipitated metal oxalates are separated by, e.g., filtration, sedimentation, or centrifugation. The filtrate, which contains the bulk of the bromine and soluble metals such as sodium, is sent to disposal. The metal oxalates can be directly recycled to the oxidation reactor, or they can be subjected to a heat soak in aqueous acetic acid to convert them to a more catalytically active form, presumably the acetates. The heat soak can be carried out in batch or continuous mode, at a temperature of about 400° to 550° F. The acetic acid contains about 1 to 20 percent water, and the weight ratio of aqueous acetic acid to metals is about 10:1 to 2000:1. The residence time is about 10 minutes to 24 hours. The resulting catalyst solution can be sent directly to the oxidation reactors.

In summary, the instant invention comprises a process for recoverying the metal components of an oxidation catalyst comprising cobalt, manganese and bromine components, or cobalt, manganese, zirconium and bromine components from an oxidation reaction to oxidize pseudocumene to trimellitic acid, which process comprises:

(a) separation of a catalyst containing residue stream from said oxidation reaction;

(b) addition of water to said catalyst residue stream to form an aqueous solution;

(c) addition of an oxalic acid compound to said aqueous solution in an amount required to precipitate from said aqueous solution said metal components of said catalyst as oxalate salts;

(d) separation of said oxalate salts from said aqueous solution;

(e) application of heat to said oxalate salts after said separation to convert said salts to more catalytically active forms of said salts.

The instant invention also comprises a process wherein said more catalytically active forms of said salts are recycled to said oxidation reaction as oxidation catalyst comonents, and wherein said residue stream from said oxidation reaction is the bottoms stream from distillation of trimellitic anhydride obtained from dehydration of total oxidation reactor effluent containing said trimellitic acid, or wherein said residue stream from said oxidation reaction comprises (a) the bottoms stream from distillation of filtrate from effluent of said oxidation reaction, said effluent subjected to filtration to remove trimellitic acid and (b) the bottoms stream from distillation of crude trimellitic anhydride obtained from dehydration of trimellitic acid filter cake from said filtration to remove said trimellitic acid, and wherein said oxalate salts are heated at a temperature of about 400° F. to about 550° F. in the presence of acetic acid, and said oxalic acid compound is selected from the group consisting of oxalic acid and metal salts of oxalic acid.

The following examples will serve to provide a fuller understanding of the invention, but it is to be understood that these examples are given for illustrative purposes only and will not be interpreted as limiting the invention in any way.

EXAMPLE 1

In a three-neck flask equipped with a heating mantle, magnetic stirrer, thermometer and reflux condenser, 200 g of distilled water were heated to the boiling point. 100 g of residue from a distillation of dehydrated total trimellitic anhydride reactor effluent were added, and the mixture was reheated to the boiling point while stirring, and allowed to homogenize. 10 g of oxalic acid dihydrate were added, and the mixture was stirred for one hour. It was then vacuum filtered through a steam-heated Buchner funnel using a house vacuum. The dried cake and the filtrate were analyzed for metals and bromine. The results are shown in Table I. Cobalt recovery was high (86 percent based on residue). Manganese recovery was distinctly lower (72 percent), and bromine and zirconium recoveries were very low (0.3 and 3.7 percent, respectively).

TABLE 1
Catalyst Recovery from TRE Residue

| Sample No. | Sample Type | | Co | Mn |
|---|---|---|---|---|
| 7614-32-1 | TRE Bottoms (100 g) | % by Weight | .76 | .230 |
| | | Weight, g | .76 | .230 |
| 7614-32-2 | Dry Cake (5.5 g) | % by Weight | 11.9 | 3.0 |
| | | Weight, g | .654 | .165 |
| | | Recovery, % | 86.1 | 71.7 |
| 7614-32-3 | Filtrate (260.8 g) | % by Weight | .0175 | .0272 |
| | | Weight, g | .0456 | .071 |
| | | Recovery, % | 6.0 | 30.9 |
| | Cake and Filtrate | Weight, g | .700 | .236 |
| | | Recovery, % | 92.1 | 102.6 |
| | | | Br | Ce |
| 7614-32-1 | TRE Bottoms (100 g) | % by Weight | .087 | .209 |
| | | Weight, g | .087 | .209 |
| 7614-32-2 | Dry Cake (5.5 g) | % by Weight | .0056 | 2.7 |
| | | Weight, g | .0003 | .148 |
| | | Recovery, % | .3 | 70.8 |
| 7614-32-3 | Filtrate (260.8 g) | % by Weight | .034 | .0042 |
| | | Weight, g | .0887 | .0110 |
| | | Recovery, % | 102.0 | 5.3 |
| | Cake and Filtrate | Weight, g | .0890 | .159 |
| | | Recovery, % | 102.3 | 76.1 |
| | | | Fe | Zr |
| 7614-32-1 | TRE Bottoms (100 g) | % by Weight | .296 | .041 |
| | | Weight, g | .296 | .041 |
| 7614-32-2 | Dry Cake (5.5 g) | % by Weight | 4.6 | .028 |
| | | Weight, g | .253 | .0015 |
| | | Recovery, % | 85.5 | 3.7 |
| 7614-32-3 | Filtrate (260.8 g) | % by Weight | .0115 | .0145 |
| | | Weight, g | .0300 | .0378 |
| | | Recovery, % | 10.1 | 92.2 |
| | Cake and Filtrate | Weight, g | .283 | .0393 |
| | | Recovery, % | 95.6 | 95.9 |

Note: TRE is Total Reactor Effluent

EXAMPLE 2

The general procedure of Example 1 was followed, but commercial plant residue (combined solvent stripper bottoms and product distillation bottoms) was used, and the ratio of water to bottoms was reduced to 1:1. The oxalic acid concentration was varied between 0 to 6 percent based on residue. The results are shown in Table II. Recovery of all catalyst components was very low, and the filtration was slow when no oxalic acid was used. At 4 percent oxalic acid (bases on residue), cobalt recovery exceeded 90 percent. Manganese recovery was again distinctly lower (66 percent). Recoveries of iron (a corrosion metal) and cerium (an optional catalyst component) were high. Recoveries of bromine, sodium (added to reduce corrosion in the solvent dehydration tower), and zirconium were low. The feed was 100 g TMA bottoms immersed in 100 g of distilled water. Oxalic acid was added as shown in Table II.

TABLE II
Catalyst Recovery from TMA Bottoms
Effect of Oxalic Acid Concentration
Feed: 100 g Commercial Plant Residue
100 g Distilled Water
Oxalic Acid Dihydrate as Indicated

| Sample No. | Sample Type | Oxalic Acid, g | | Co | Mn |
|---|---|---|---|---|---|
| 7614-34-1 (WJ 3686) | TMA Bottoms (100 g) | | % by Weight | 1.02 | .235 |
| | | | Weight, g | 1.02 | .235 |
| 7614-35-1 | Dry Cake (4.85 g) | 0 | % by Weight | .62 | .138 |
| | | | Weight, g | .0301 | .0067 |
| | | | Recovery, % | 3.0 | 2.9 |
| 7614-35-2 | Dry Cake (8.8 g) | 2 | % by Weight | 7.8 | .71 |
| | | | Weight, g | .686 | .0625 |
| | | | Recovery, % | 67.3 | 26.6 |
| 7614-36-1 | Dry Cake (10.75 g) | 4 | % by Weight | 8.7 | 1.44 |
| | | | Weight, g | .935 | .155 |
| | | | Recovery, % | 91.7 | 65.9 |
| 7614-36-2 | Dry Cake (10.0 g) | 6 | % by Weight | 9.7 | 1.86 |
| | | | Weight, g | .97 | .186 |
| | | | Recovery, % | 95.1 | 79.1 |
| | | | | Br | Ce |
| 7614-34-1 (WJ 3686) | Plant Bottoms (100 g) | | % by Weight | .91 | .170 |
| | | | Weight, g | .91 | .170 |
| 7614-35-1 | Dry Cake (4.85 g) | 0 | % by Weight | .55 | .118 |
| | | | Weight, g | .0267 | .0057 |
| | | | Recovery, % | 2.9 | 3.4 |
| 7614-35-2 | Dry Cake (8.8 g) | 2 | % by Weight | .396 | 1.03 |
| | | | Weight, g | .0348 | .0906 |
| | | | Recovery, % | 3.8 | 53.3 |
| 7614-36-1 | Dry Cake (10.75 g) | 4 | % by Weight | .387 | 1.37 |
| | | | Weight, g | .0416 | .147 |
| | | | Recovery, % | 4.6 | 86.6 |
| 7614-36-2 | Dry Cake (10.0 g) | 6 | % by Weight | .285 | 1.54 |
| | | | Weight, g | .0285 | .154 |
| | | | Recovery, % | 3.1 | 90.6 |
| | | | | Fe | Na |
| 7614-34-1 (WJ 3686) | TMA Bottoms (100 g) | | % by Weight | .0115 | .228 |
| | | | Weight, g | .0115 | .228 |
| 7614-35-1 | Dry Cake (4.85 g) | 0 | % by Weight | .0102 | .183 |
| | | | Weight, g | .0005 | .0089 |
| | | | Recovery, % | 4.3 | 3.9 |
| 7614-35-2 | Dry Cake (8.8 g) | 2 | % by Weight | .079 | .130 |
| | | | Weight, g | .0070 | .0114 |
| | | | Recovery, % | 60.5 | 5.0 |
| 7614-36-1 | Dry Cake (10.75 g) | 4 | % by Weight | .100 | .144 |
| | | | Weight, g | .0108 | .0155 |
| | | | Recovery, % | 93.5 | 6.8 |
| 7614-36-2 | Dry Cake (10.0 g) | 6 | % by Weight | .099 | .117 |
| | | | Weight, g | .0099 | .0117 |
| | | | Recovery, % | 86.1 | 5.1 |
| | | | | | Zr |
| 7614-34-1 (WJ 3686) | TMA Bottoms (100 g) | | % by Weight | | .047 |
| | | | Weight, g | | .047 |
| 7614-35-1 | Dry Cake (4.85 g) | 0 | % by Weight | | .031 |
| | | | Weight, g | | .0015 |
| | | | Recovery, % | | 3.2 |
| 7614-35-2 | Dry Cake (8.8 g) | 2 | % by Weight | | .046 |
| | | | Weight, g | | .0040 |
| | | | Recovery, % | | 8.6 |
| 7614-36-1 | Dry Cake (10.75 g) | 4 | % by Weight | | .087 |
| | | | Weight, g | | .0094 |
| | | | Recovery, % | | 19.9 |
| 7614-36-2 | Dry Cake (10.0 g) | 6 | % by Weight | | .074 |
| | | | Weight, g | | .0074 |
| | | | Recovery, % | | 15.7 |

EXAMPLE 3

Table III shows results obtained with the addition of chelating agents during oxalate precipitation, in an effort to solubilize the iron. The feed was 200 g TMA residue, 200 g distilled water, and 6 g oxalic acid dihydrate.

TABLE III

Catalyst Recovery with Added Chelating Agents

| Sample No. | Sample Type | Additive | | Co | Mn |
|---|---|---|---|---|---|
| 7614-51-5 | Feed (200 g) | | % by Weight | .88 | .207 |
| | | | Weight, g | 1.76 | .414 |
| 7614-51-1 | Dry Cake (13.6 g) | 0.3 g EDTA | % by Weight | 11.2 | 1.79 |
| | | | Weight, g | 1.52 | .243 |
| | | | Recovery, % | 86.5 | 58.8 |
| 7614-51-3 | Dry Cake (13.8 g) | 0.3 g NTA | % by Weight | 12.0 | 1.99 |
| | | | Weight, g | 1.66 | .275 |
| | | | Recovery, % | 94.1 | 66.3 |
| 7614-51-4 | Dry Cake (14.2 g) | | % by Weight | 11.9 | 1.89 |
| | | | Weight, g | 1.690 | .268 |
| | | | Recovery, % | 96.0 | 64.8 |
| | | | | Br | Ce |
| 7614-51-5 | Feed (200 g) | | % by Weight | .91 | .155 |
| | | | Weight, g | 1.82 | .31 |
| 7614-51-1 | Dry Cake (13.6 g) | 0.3 g EDTA | % by Weight | .326 | 1.94 |
| | | | Weight, g | .0443 | .264 |
| | | | Recovery, % | 2.44 | 85.1 |
| 7614-51-3 | Dry Cake (13.8 g) | 0.3 g NTA | % by Weight | .319 | 1.84 |
| | | | Weight, g | .0440 | .254 |
| | | | Recovery, % | 2.42 | 81.9 |
| 7614-51-4 | Dry Cake (14.2 g) | | % by Weight | .358 | 1.99 |
| | | | Weight, g | .0508 | .283 |
| | | | Recovery, % | 2.80 | 91.2 |
| | | | | Cr | Cu |
| 7614-51-5 | Feed (200 g) | | % by Weight | .0030 | .0006 |
| | | | Weight, g | .0060 | .0012 |
| 7614-51-1 | Dry Cake (13.6 g) | 0.3 g EDTA | % by Weight | .0062 | .0012 |
| | | | Weight, g | .00084 | .00016 |
| | | | Recovery, % | 14.1 | 13.6 |
| 7614-51-3 | Dry Cake (13.8 g) | 0.3 g NTA | % by Weight | .0051 | .0009 |
| | | | Weight, g | .00070 | .00012 |
| | | | Recovery, % | 11.7 | 10.4 |
| 7614-51-4 | Dry Cake (14.2 g) | | % by Weight | .0038 | .0021 |
| | | | Weight, g | .00054 | .00030 |
| | | | Recovery, % | 9.0 | 24.8 |
| | | | | Fe | La |
| 7614-51-5 | Feed (200 g) | | % by Weight | .011 | .088 |
| | | | Weight, g | .022 | .176 |
| 7614-51-1 | Dry Cake (13.6 g) | 0.3 g EDTA | % by Weight | .133 | .93 |
| | | | Weight, g | .0181 | .126 |
| | | | Recovery, % | 82.2 | 71.9 |
| 7614-51-3 | Dry Cake (13.8 g) | 0.3 g NTA | % by Weight | .136 | .91 |
| | | | Weight, g | .0188 | .126 |
| | | | Recovery, % | 85.3 | 71.4 |
| 7614-51-4 | Dry Cake (14.2 g) | | % by Weight | .146 | .98 |
| | | | Weight, g | .0207 | .139 |
| | | | Recovery, % | 94.2 | 79.1 |
| | | | | Mo | Na |
| 7614-51-5 | Feed (200 g) | | % by Weight | .0012 | .228 |
| | | | Weight, g | .0024 | .456 |
| 7614-51-1 | Dry Cake (13.6 g) | 0.3 g EDTA | % by Weight | .0034 | .131 |
| | | | Weight, g | .00046 | .0178 |
| | | | Recovery, % | 19.3 | 3.9 |
| 7614-51-3 | Dry Cake (13.8 g) | 0.3 g NTA | % by Weight | .0049 | .128 |
| | | | Weight, g | .00068 | .0177 |
| | | | Recovery, % | 28.2 | 3.9 |
| 7614-51-4 | Dry Cake (14.2 g) | | % by Weight | .0040 | .101 |
| | | | Weight, g | .00057 | .0143 |
| | | | Recovery, % | 23.7 | 3.1 |
| | | | | Ni | Ti |
| 7614-51-5 | Feed (200 g) | | % by Weight | .0050 | .0006 |
| | | | Weight, g | .01 | .0012 |
| 7614-51-1 | Dry Cake (13.6 g) | 0.3 g EDTA | % by Weight | .0600 | .0029 |
| | | | Weight, g | .00816 | .00039 |
| | | | Recovery, % | 81.6 | 32.9 |
| 7614-51-3 | Dry Cake (13.8 g) | 0.3 g NTA | % by Weight | .0740 | .0032 |
| | | | Weight, g | .0102 | .00044 |

TABLE III-continued

Catalyst Recovery with Added Chelating Agents

| Sample No. | Sample Type | Additive | | | |
|---|---|---|---|---|---|
| | | | Recovery,% | 102.1 | 36.8 |
| 7614-51-4 | Dry Cake (14.2 g) | | % by Weight | .0720 | .0035 |
| | | | Weight, g | .0102 | .00050 |
| | | | Recovery,% | 102.2 | 41.4 |
| | | | | Y | Zr |
| 7614-51-5 | Sample Feed (200 g) | | % by Weight | .0040 | .052 |
| | | | Weight, g | .008 | .104 |
| 7614-51-1 | Dry Cake (13.6 g) | 0.3 g EDTA | % by Weight | .045 | .078 |
| | | | Weight, g | .0061 | .0106 |
| | | | Recovery,% | 76.5 | 10.2 |
| 7614-51-3 | Dry Cake (13.8 g) | 0.3 g NTA | % by Weight | .042 | .065 |
| | | | Weight, g | .0058 | .0090 |
| | | | Recovery,% | 72.4 | 8.6 |
| 7614-51-4 | Dry Cake (14.2 g) | | % by Weight | .045 | .085 |
| | | | Weight, g | .0064 | .0121 |
| | | | Recovery,% | 79.9 | 11.6 |

EXAMPLE 4

Table IV shows a comparison of an unwashed precipitate with one which was reslurried with boiling water and refiltered. A large amount of material, mostly soluble organics, was washed off. Some manganese and zirconium was also washed off. Recovery of cobalt remained essentially quantitative. The feed comprised 200 grams of TMA residue and 200 g of distilled water.

TABLE IV

Effect of Washing Reclaimed Catalyst
Feed: 200 g Commercial Plant Residue
200 g Distilled Water
7 g Oxalic Acid Dihydrate

| Sample No. | Sample Type | | Co | Mn |
|---|---|---|---|---|
| 7614-51-5 (WJ3686) | Feed (200 g) | % by Weight | .88 | .207 |
| | | Weight, g | 1.76 | .414 |
| 7614-94-2 | Dried Cake (17.2 g) | % by Weight | 10.4 | 1.82 |
| | | Weight, g | 1.79 | .313 |
| | | Recovery, % | 101.6 | 75.6 |
| 7614-94-1 | Washed Cake* (9.1 g) | % by Weight | 19.9 | 2.83 |
| | | Weight, g | 1.81 | .258 |
| | | Recovery, % | 102.9 | 62.2 |
| | | | Ce | Cr |
| 7614-51-5 (WJ3686) | Feed (200 g) | % by Weight | .155 | .0030 |
| | | Weight, g | .31 | .0060 |
| 7614-94-2 | Dried Cake (17.2 g) | % by Weight | 1.79 | .0042 |
| | | Weight, g | .308 | .0007 |
| | | Recovery, % | 99.3 | 12.4 |
| 7614-94-1 | Washed Cake* (9.1 g) | % by Weight | 3.33 | .0090 |
| | | Weight, g | .303 | .0008 |
| | | Recovery, % | 97.8 | 13.6 |
| | | | Cu | Fe |
| 7614-51-5 (WJ3686) | Feed (200 g) | % by Weight | .0006 | .011 |
| | | Weight, g | .0012 | .022 |
| 7614-94-2 | Dried Cake (17.2 g) | % by Weight | .0026 | .11 |
| | | Weight, g | .0004 | .019 |
| | | Recovery, % | 37.3 | 86.0 |
| 7614-94-1 | Washed Cake* (9.1 g) | % by Weight | .0115 | .20 |
| | | Weight, g | .0010 | .018 |
| | | Recovery, % | 87.2 | 82.7 |
| | | | La | Mo |
| 7614-51-5 (WJ3686) | Feed (200 g) | % by Weight | .0880 | .0012 |
| | | Weight, g | .176 | .0024 |
| 7614-94-2 | Dried Cake (17.2 g) | % by Weight | .97 | .0044 |
| | | Weight, g | .167 | .0008 |
| | | Recovery, % | 94.8 | 31.5 |
| 7614-94-1 | Washed Cake* (9.1 g) | % by Weight | 1.83 | .0075 |
| | | Weight, g | .166 | .0007 |
| | | Recovery, % | 94.6 | 28.4 |
| | | | Na | Ni |
| 7614-51-5 | Feed | % by Weight | .228 | .0050 |

TABLE IV-continued
Effect of Washing Reclaimed Catalyst
Feed: 200 g Commercial Plant Residue
200 g Distilled Water
7 g Oxalic Acid Dihydrate

| Sample No. | Sample Type | | | |
|---|---|---|---|---|
| (WJ3686) | (200 g) | Weight, g | .456 | .01 |
| 7614-94-2 | Dried Cake | % by Weight | .086 | .077 |
| | (17.2 g) | Weight, g | .015 | .013 |
| | | Recovery, % | 3.2 | 132.4 |
| 7614-94-1 | Washed Cake* | % by Weight | <.01 | .157 |
| | (9.1 g) | Weight, g | <.001 | .014 |
| | | Recovery, % | <.2 | 142.9 |
| | | | Ti | Y |
| 7614-51-5 | Feed | % by Weight | .0006 | .0040 |
| (WJ3686) | (200 g) | Weight, g | .0012 | .008 |
| 7614-94-2 | Dried Cake | % by Weight | .0027 | .040 |
| | (17.2 g) | Weight, g | .0005 | .007 |
| | | Recovery, % | 38.7 | 86.0 |
| 7614-94-1 | Washed Cake* | % by Weight | .0054 | .081 |
| | (9.1 g) | Weight, g | .0005 | .0074 |
| | | Recovery, % | 41.0 | 92.1 |
| | | | Zr | |
| 7614-51-5 | Feed | % by Weight | .052 | |
| (WJ3686) | (200 g) | Weight, g | .104 | |
| 7614-94-2 | Dried Cake | % by Weight | .15 | |
| | (17.2 g) | Weight, g | .026 | |
| | | Recovery, % | 24.8 | |
| 7614-94-1 | Washed Cake* | % by Weight | .19 | |
| | (9.1 g) | Weight, g | .017 | |
| | | Recovery, % | 16.6 | |

*Reslurried in 200 g boiling water, filtered and dried.

EXAMPLE 5

Pseudocumene oxidations were performed in which some of the virgin catalyst was replaced by reclaimed catalyst. Tailout catalyst was added continuously to the reactor in the last 20–30 minutes. The results are listed in Table V. Compared to the base case (8046-28), a 50 percent cobalt replacement gave a normal oxidation. Replacements of 75 percent (8046-196) and 90 percent (8046-190) gave good product, but run times were longer and hydrocarbon burning was higher, indicating that the recycled catalyst is somewhat less active than virgin catalyst. Analysis for methyl dibasics (Me Dibasics) in the product analysis is a measure of reaction intermediates which indicates how complete the reaction is. The lesser presence of methyl dibasics indicates a more complete reaction.

TABLE V
Pseudocumene Oxidations with Reclaimed Catalyst

Initial Catalyst (wt. % of PSC): 0.182 Co, 0.068 Mn, 0.270 Br, 0.004 Zr
Tailout Catalyst (wt. % of PSC): 0.010 Mn, 0.005 Zr
Solvent Ratio: 1.87
Temperature Profile: 320° F. Initial; 410° F. Final

| Run No. | Reclaimed Catalyst | | Replacement of Initial Catalyst, % | | | |
|---|---|---|---|---|---|---|
| | Sample No. | g | Co | Mn | Br | Zr |
| 8046-28 | — | — | — | — | — | — |
| 8046-148 | 7514-36-1 | 2.35 | 50 | 31 | 1.5 | 23 |
| 8046-190 | 7614-36-1 | 3.79 | 90 | 65 | 1.8 | 31 |
| 8046-196 | 7614-36-1 | 2.00 | 75 | 50 | 1.9 | 30 |
| | 7614-36-2 | 1.37 | | | | |
| 8336-6 | 7614-40-1 | 2.52 | 90 | 68 | 1.1 | 19 |
| 8336-102 | 7614-40-1 | 2.52 | 90 | 68 | 1.1 | 19 |
| 8336-116 | Co Oxalate | 1.15 | 90 | — | — | — |
| 8336-151 | 7614-99-1 | 1.85 | 90 | 48 | | 39 |
| 8336-153 | 7614-94-2 | 3.54 | 90 | 60 | | 59 |
| 8336-169 | 7614-94-2 | 3.54 | 90 | 60 | | 59 |

| Run No. | Comments | Pretreatment Temp., °F. |
|---|---|---|
| 8046-28 | Base Run to 17% O$_2$ | — |
| 8046-148 | | — |
| 8046-190 | | — |
| 8046-196 | | — |
| 8336-6 | Added .04% Mn + .006% Zr | |
| 8336-102 | Mn + .006% Zr | 400 |
| 8336-108 | Added Corrosion Metals | — |
| 8336-109 | Base Run to 14% O$_2$ | — |
| 8336-116 | Added Authentic Co Oxalate | 400 |
| 8336-151 | Washed Reclaimed Catalyst | 400 |
| 8336-153 | | 500 |
| 8336-169 | | 450 |

| | Product Analyses, % of Dried Solids | | |
|---|---|---|---|
| Run No. | Me Dibasics | Total Low Boilers | High Boilers |
| 8046-28 | .38 | 2.75 | 2.66 |
| 8046-148 | .30 | 2.42 | 1.71 |
| 8046-190 | .31 | 2.81 | 2.29 |
| 8046-196 | .30 | 2.70 | 2.35 |
| 8336-6 | .28 | 2.69 | 1.98 |
| 8336-102 | .36 | 2.63 | 1.92 |
| 8336-108 | .32 | 2.21 | 1.46 |
| 8336-109 | .28 | 2.12 | 2.74 |
| 8336-116 | | | |
| 8336-151 | .24 | 2.81 | 1.99 |
| 8336-153 | .57 | 3.17 | 1.59 |
| 8336-169 | .37 | 2.63 | 1.55 |

| | Product Analyses, % of Dried Solids | | |
|---|---|---|---|
| Run No. | TMLA | Fe | CO$_x$, % of HC |
| 8046-28 | 91.65 | | 5.7 |
| 8046-148 | 92.6 | .0015 | 6.1 |
| 8046-190 | 90.3 | .0015 | 7.3 |
| 8046-196 | 90.4 | .0018 | 7.2 |
| 8336-6 | 92.1 | .0016 | 7.5 |
| 8336-102 | 89.9 | .0045 | 7.4 |
| 8336-108 | 94.0 | .0025 | 5.1 |
| 8336-109 | 90.1 | .0017 | 6.0 |
| 8336-116 | | | 6.4 |
| 8336-151 | 89.5 | .0031 | 6.9 |
| 8336-153 | 86.4 | .0066 | 5.5 |
| 8336-169 | 91.5 | .0053 | 5.5 |

| | Run Time, min | |
|---|---|---|
| Run No. | to 14 % O2 | to 17 % O2 |
| 8046-28 | 66 | 74 |
| 8046-148 | 64 | 72 |
| 8046-190 | 71 | 78 |
| 8046-196 | 71 | 79 |
| 8336-6 | 68 | 77 |
| 8336-102 | 71 | 80 |
| 8336-108 | 68 | 75 |
| 8336-109 | 73 | |
| 8336-116 | 67 | |
| 8336-151 | 73 | |
| 8336-153 | 70 | |
| 8336-169 | 66 | |

EXAMPLE 6

Addition of extra manganese and zirconium to an oxidation with reclaimed catalyst (8036-6) gave no improvement, suggesting that it is the recycled cobalt which is in a less active form.

EXAMPLE 7

Addition of six corrosion metals at ten times the level found in the reclaimed catalyst (Table VI) gave a good oxidation (8336-108), indicating that corrosion metals are not the cause of the low activity of the reclaimed catalyst.

TABLE VI

Added Corrosion Metals for Oxidation Run 8336-108

| Compound | Metal Content, percent | Added to Oxidation* | |
|---|---|---|---|
| | | Compound, mg | Metal, ppm of PSC |
| Iron (III) acetate hydroxide, dibasic | 29.3 | 191 | 248 |
| Ammonium Molybdate | 54.3 | 2.8 | 6.8 |
| Chromium (III) Acetate | 21.0 | 6.9 | 6.4 |
| Cupric Acetate | 31.8 | 2.5 | 3.6 |
| Nickel (II) Acetate | 23.6 | 114 | 122 |
| Titanium (IV) oxide bis (acac) | 18.3 | 7.3 | 5.9 |

*Based on 225 g pseudocumene.

EXAMPLE 8

Pretreatment of reclaimed catalyst at 400° F. in acetic acid did not improve the oxidation, both for unwashed (8336-102) and washed (8336-151) catalyst. Authentic cobalt oxalate gave a better oxidation (8336-116), suggesting that not all the reclaimed catalyst is present as the oxalate.

EXAMPLE 9

Two samples of reclaimed catalyst were examined by X-ray diffraction. There was a major phase (about 62–86 percent) of cobalt oxalate and a minor unidentified phase. Apparently, some other ligands are present, such as aromatic acids.

EXAMPLE 10

Two oxidations were performed with reclaimed catalyst pretreated at 450° F. (8336-169) and 500° F. (8336-153) in acetic acid. These oxidations gave low hydrocarbon burning, indicating that the unknown ligands had been replaced by acetic acid.

What is claimed is:

1. A process for recovering the metal components of an oxidation catalyst comprising cobalt, manganese and bromine components, or cobalt, manganese, zirconium and bromine components from an oxidation reaction to oxidize pseudocumene to trimellitic acid, which process comprises:
   a. separation of a catalyst containing residue stream from said oxidation reaction;
   b. addition of water to said catalyst residue stream to form an aqueous solution;
   c. addition of an oxalic acid compound to said aqueous solution in an amount required to precipitate from said aqueous solution said metal components of said catalyst as oxalate salts;
   d. separation of said oxalate salts from said aqueous solution;
   e. application of heat to said oxalate salts after said separation to convert said salts to more catalytically active forms of said salts.

2. The process of claim 1 wherein said more catalytically active forms of said salts are recycled to said oxidation reaction as oxidation catalyst components.

3. The process of claim 1 wherein said residue stream from said oxidation reaction is the bottoms stream from distillation of trimelletic anhydride obtained from dehydration of total oxidation reactor effluent containing said trimellitic acid.

4. The process of claim 1 wherein said residue stream from said oxidation reaction comprises (a) the bottoms stream from distillation of filtrate from effluent of said oxidation reaction, said effluent subjected to filtration to remove trimellitic acid and (b) the bottoms stream from distillation of crude trimellitic anhydride obtained from dehydration of trimellitic acid filter cake from said filtration to remove said trimellitic acid.

5. The process of claim 1 wherein said oxalate salts are heated at a temperature of about 400° F. to about 550° F. in the presence of acetic acid.

6. The process of claim 1 wherein said oxalic acid compound is selected from the group consisting of oxalic acid and metal salts of oxalic acid.

* * * * *

UNITED STATES PATENT OFFICE
CERTIFICATE OF CORRECTION

Patent No. 4,786,752                     Dated November 22, 1988

Inventor(s) Holzhauer, Schammel and Nowicki

It is certified that error appears in the above-identified patent and that said Letters Patent is hereby corrected as shown below:

| PATENT Column | Line | |
|---|---|---|
| Title Column | 2 | "PSEUDOCUMENT" should read --PSEUDOCUMENE-- |
| 1 | 2 | "PSEUDOCUMENT" should read --PSEUDOCUMENE-- |
| 1 | 58 | "$C_2-C_{16}$" should read --$C_2-C_6$-- |
| 2 | 67 | "liquid phase" should read --liquid-phase-- |
| 4 | 11 | "recoverying" should read --recovering-- |
| 4 | 33 | "comonents" shouls read --components-- |
| 5 | 45 | "to" should read --and-- |
| 5 | 49 | "(bases" should read --(based-- |

Signed and Sealed this

First Day of August, 1989

Attest:

DONALD J. QUIGG

Attesting Officer

Commissioner of Patents and Trademarks